(12) United States Patent
Ruangwattanasuk

(10) Patent No.: US 11,129,899 B1
(45) Date of Patent: Sep. 28, 2021

(54) METHOTREXATE DERIVATIVES AND USES THEREOF

(71) Applicants: S.S. Manufacturing Co., Ltd, Nonthaburi (TH); Ornin Ruangwattanasuk, Bangkok (TH)

(72) Inventor: Ornin Ruangwattanasuk, Bangkok (TH)

(73) Assignee: S.S. MANUFACTURING CO., LTD., Nonthaburi (TH)

( * ) Notice: Subject to any disclaimer, the term of this patent is extended or adjusted under 35 U.S.C. 154(b) by 0 days.

(21) Appl. No.: 17/212,137

(22) Filed: Mar. 25, 2021

(51) Int. Cl.
*A61K 31/519* (2006.01)
*A61K 47/54* (2017.01)

(52) U.S. Cl.
CPC .......... *A61K 47/554* (2017.08); *A61K 31/519* (2013.01)

(58) Field of Classification Search
CPC combination set(s) only.
See application file for complete search history.

*Primary Examiner* — Heidi Reese
(74) *Attorney, Agent, or Firm* — Moser Taboada

(57) ABSTRACT

A pharmaceutical compound is provided. The pharmaceutical compound includes a first component as methrotrexate and a second component as cholesterol, wherein the first component is covalently conjugated to the second component having a structure represented by the following chemical formula (I):

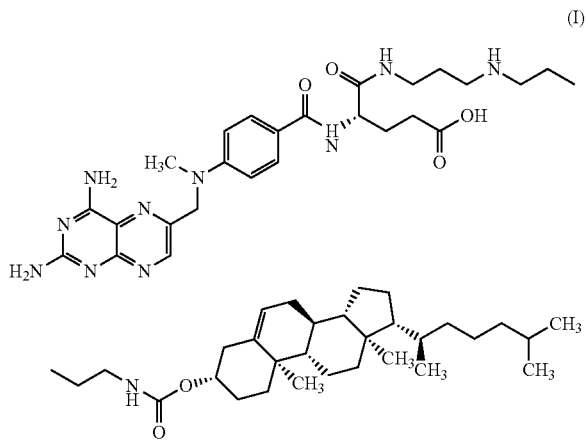

(I)

wherein α carboxyl group of methrotrexate is conjugated to cholesterol using spermidine as a linker.

20 Claims, 4 Drawing Sheets

METHOTREXATE DERIVATIVES AND USES THEREOF

FIELD OF THE INVENTION

This invention relates to Methotrexate derivatives and the uses thereof.

BACKGROUND OF THE INVENTION

The modification of pharmaceuticals to achieve one or more desirable properties of the parent drug has been studied and applied to many compounds in clinical use today. The modified forms are often intended to alter the absorption, metabolism, excretion, tissue distribution, toxicity, and activity of the parent compound in a desirable way. Additionally, drug modifications have been made to some compounds with the goal of creating a drug that is selectively activated or deactivated in a target tissue in order to increase the specificity of the intended drug effects while decreasing the unintended side effects associated with the parent compound. The modified-drug approach has been applied to some of the most successful antibiotics and chemotherapeutic compounds that are designed to be toxic to some living cells and simultaneously non-toxic or much less toxic to other populations of living cells.

Methotrexate (MTX), ((2S)-2-[(4-{[(2,4-diaminopteridin-6-yl)methyl](methyl)amino}phenyl)formamido]pentanedioic acid), (CAS 59-05-2), is an antimetabolite drug, that is widely used as an effective anticancer agent and immunosuppressant (1,2). Several MTX derivatives have been constructed to date in which those derivatives have demonstrated additional different properties when compared to MTX (3,4). Although several derivatives have been found to exhibit greater cytotoxicity than the clinically used MTX, a concomitant increase in systemic toxicity is also commonly observed. It has been known that inhibition of Dihydrofolate reductase enzyme (DHFR), the key enzyme of purine metabolism and thereby DNA synthesis, is the major action of MTX (1). Following the administration, MTX distributes mainly in non-fatty tissue and does not cross the blood brain barrier. Several physicochemical reports show that MTX is poorly dissolved in oil (5). It has been known that fat-soluble drug distributes better in fat tissue than water-soluble drug. Based on the current advance in lipid delivery drug system, fat-soluble derivative of MTX may extend the therapeutic scope (6).

Bio-conjugation is a process used to attach a bioactive molecule to another molecule via a covalent bond which leads to the formation of a novel chemical structure which may have enhanced properties compared to those of the original molecule (7). While this process or method has been known, there has not been an attempt in synthesizing a derivative that is capable of functioning as per the need as above mentioned.

REFERENCES (1) Bedoui Y, Guillot X, Sélambarom J, Guiraud P, Giry C, Jaffar-Bandjee M C, Ralandison S, Gasque P. Methotrexate an old drug with new trick. *Int J Mol Sci.* 20:5023.
(2) Visentin M, Zhao R, Goldman I D. The antifolates. *Hematol Oncol Clin North Am.* 26-629-648.
(3) Sirotnak F M, DeGraw J I, Moccio D M, Samuels L L, Goutas U. New folate analogs of the 10-deaza-aminopterin series. Basis for structural design and biochemical and pharmacologic properties. *Cancer Chemother Pharmacol.* 1984; 12:18-25.
(4) Tamura T, Higuchi Y, Kitamura H, Murao N, Saitoh R, Morikawa T, Sato H. Novel hyaluronic acid-methotrexate conjugate suppresses joint inflammation in the rat knee: efficacy and safety evaluation in two rat arthritis models
(5) Kim D S, Cho J H, Park J H, Kim J S, Song E S, Kwon J, Giri B R, Jin S G, Kim K S, Choi H G, Kim D W. Self-microemulsifying drug delivery system (SMEDDS) for improved oral delivery and photostability of methotrexate. *Int J Nanomedicine.* 2019 5; 14:4949-4960. doi: 10.2147/IJN.S211014. eCollection 2019
(6) Moura J A, Valduga C J, Tavares E R, Kretzer I F, Maria D A, Maranhão R C. Novel formulation of a methotrexate derivative with a lipid nanoemulsion. *Int J Nanomedicine.* 2011; 6: 2285-2295.
(7) Chaikomon K, Chattong S, Chaiya T, et al. Doxorubicin-conjugated dexamethasone induced MCF-7 apoptosis without entering the nucleus and able to overcome MDR-1-induced resistance. *Drug Des Devel Ther.* 2018; 12:2361-2369.

SUMMARY OF THE INVENTION

This invention relates to the molecule and methods of treating diseases and disorders utilizing a new derivative of MTX that was derived via conjugation of the α carboxyl group of MTX to the 3p-hydroxyl group of cholesterol, (CAS 57-88-5), (3β-Hydroxy-5-cholestene, 5-Cholesten-3β-ol), (CAS 57-88-5), using spermidine, ((4-aminobutyl)(3-aminopropyl)amine), (CAS 124-20-9) as a linker, having the compound formula as (4S)-4-{[3-({4-[({[(1R,3aS,3bS,7S,9aR,9bS,11aR)-9a,11a-dimethyl-1-[(2R)-6-methylheptan-2-yl]-1H,2H,3H,3aH,3bH,4H,6H,7H,8H,9H,9aH,9bH,10H,11H,11aH-cyclopenta[a]phenanthren-7-yl]oxy}carbonyl)amino]butyl}amino)propyl]carbamoyl}-4-[(4-{[(2,4-diaminopteridin-6-yl)methyl](methyl)amino}phenyl)formamido]butanoic acid. In one aspect, pharmaceutical compositions comprising the disclosed compound cover an enantiomer of the said compound and pharmaceutically acceptable polymorphs, prodrugs, hydrates, solvates, salts, hydrates, clathrates, and solvates thereof.

The conjugated product rapidly inhibits DHFR enzymes and thus can address the aforementioned needs. Thus, the primary objective of use is for cancer and autoimmune disease treatment. Cancers in this case include, but are not limited to, cancer of the head, thyroid, neck, eye, skin, mouth, throat, esophagus, chest, heart, bone, blood, bone marrow, lung, colon, sigmoid, rectum, stomach, prostate, breast, ovaries, kidney, liver, pancreas, brain, intestine, heart, adrenal, subcutaneous tissue, lymph nodes, heart, and combinations thereof. More specifically, specific types of cancers that can be treated using this compound include multiple myeloma, malignant melanoma, malignant glioma, lymphoma, leukemia, and solid tumors. Autoimmune disease in the case include, but are not limited to, Adult Still's disease, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune pancreatitis, Autoimmune retinopathy, Autoimmune urticaria, Axonal & neuronal neuropathy (AMAN), Behcet's disease, Benign mucosal pemphigoid, Bullous pemphigoid, Castleman disease (CD), Celiac disease, Chagas disease, Chronic inflammatory demyelinating polyneuropathy (CIDP), Churg-Strauss Syndrome (CSS) or Eosinophilic Granulomatosis (EGPA), Cicatricial pemphigoid, Crohn's disease, Dermatitis herpetiformis, Dermatomyositis, Devic's disease (neuromyelitis optica), Discoid lupus, Erythema nodosum, Essential mixed cryoglobulinemia, Fibromyalgia, Fibrosing alveolitis, Giant cell arteritis (temporal arteritis), Giant cell myocarditis, Glomerulonephritis, Goodpasture's syndrome, Granulomatosis with Polyangiitis, autoimmune hemolytic anemia, Henoch-Schonlein purpura (HSP), pemphigoid gestationis (PG), Hidradenitis Suppurativa (HS) (Acne Inversa), IgA Nephropathy, IgG4-related sclerosing disease, Immune thrombocytopenic purpura (ITP), Inclusion body myositis (IBM), Interstitial cystitis (IC), Juvenile arthritis, Juvenile myositis (JM), Kawasaki disease, Leukocytoclastic vasculitis, Lichen planus, Lichen sclerosus, Ligneous conjunctivitis, Linear IgA disease (LAD), Systemic lupus erythematosus (SLE), Lyme disease chronic, Microscopic polyangiitis (MPA), Mixed connective tissue disease (MCTD), Multifocal Motor Neuropathy (MMN) or MMNCB, Multiple sclerosis(MS), Myasthenia gravis, Neonatal Lupus, Neuromyelitis optica, Neutropenia, Ocular cicatricial pemphigoid, Optic neuritis, Palindromic rheumatism (PR), Pemphigus, Pemphigoid, Peripheral neuropathy, Perivenous encephalomyelitis, Polyarteritis nodosa, Polymyalgia rheumatica, Polymyositis, Primary biliary cirrhosis, Primary sclerosing cholangitis, Progesterone dermatitis, Psoriasis, Psoriatic arthritis, Pyoderma gangrenosum, Raynaud's phenomenon, Reactive Arthritis, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Takayasu's arteritis, Temporal arteritis/Giant cell arteritis, Thrombocytopenic purpura (TTP), Transverse myelitis, Ulcerative colitis (UC), Undifferentiated connective tissue disease (UCTD), Uveitis, Vasculitis, Vitiligo, Vogt-Koyanagi-Harada Disease. The compound can be used for treatment (inclusive of amelioration (inclusive of prophylactically ameliorating) and prevention) of the indications recited in this application, and any for which methotrexate has effect in vivo or an appropriate screening test or animal model.

The conjugated product shows higher solubility in fat solvent therefore the application of use may suitable for but are not limited to an emulsion formulation, lipid delivery system, topical formulation and chemoembolization.

The invention has broad applicability to many different therapeutic drugs, as well as to a variety of diseases and conditions. In the other aspect, the stereometically pure disclosed compound is also useful in the treatment or prevention of microbial infections or the symptoms of microbial infections including, but not limited to, bacterial infections, fungal infections, parasitic infection, malaria, mycobacterial infection, and opportunistic infections resulting from HIV.

Some embodiments disclosed herein relate to a pharmaceutical compound comprising a first component as methotrexate and a second component as cholesterol, wherein the first component is covalently conjugated to the second component having a structure represented by the following chemical formula (I):

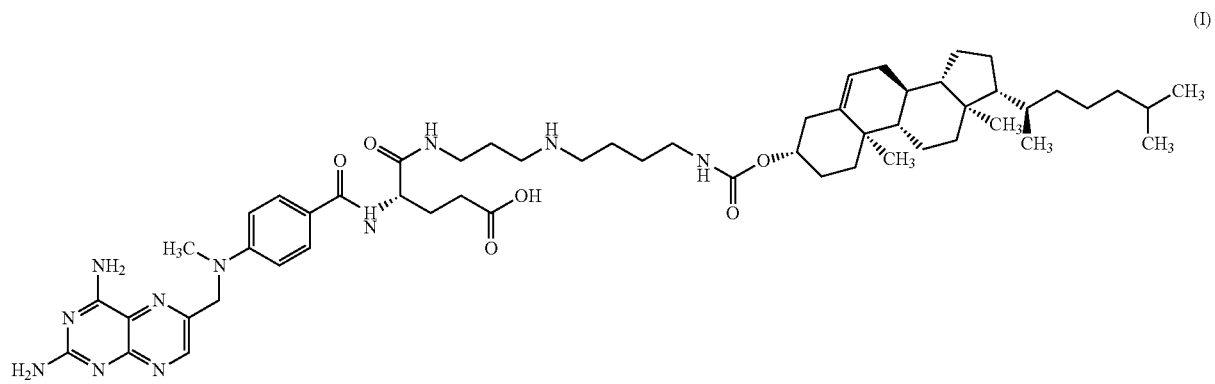 [SMILES: CC(C)CCC[C@@H](C)[C@H]1CC[C@H]2[C@@H]3CC=C4C[C@@H](OC(=O)NCCCCNCCCNC(=O)[C@H](CCC(=O)O)NC(=O)c5ccc(N(C)Cc6cnc7nc(N)nc(N)c7n6)cc5)CC[C@]4(C)[C@H]3CC[C@]12C]

(I)

wherein the α carboxyl group of methrotrexate is conjugated to cholesterol using spermidine as a linker.

Some embodiments disclosed herein relate to a pharmaceutical compound comprising a compound as defined above and a pharmaceutically acceptable carrier, excipient and/or adjuvant.

Some embodiments disclosed herein relate to use of the compound as defined above in medicine, such as the use of the embodied compound in a medicament. In some embodiments disclosed herein, the medicament including the compound as defined herein is suitable for treating mammals, such as a human.

Some embodiments disclosed herein relate to use of the compound as defined above for the manufacture of a medicament for the treatment of a cancer comprising cancer cells. Examples of the cancer include breast cancer, lung cancer, multiple myeloma, malignant melanoma, malignant glioma, lymphoma, leukemia, or other hematologic malignancy.

Some embodiments disclosed herein relate to use of the compound as defined above for the manufacture of a medicament for the treatment of an autoimmune disease. Examples of the autoimmune disease include rheumatoid arthritis, systemic lupus erythematosus (SLE), psoriasis, pemphigus, pemphigoid, sarcoidosis, vitiligo.

BRIEF DESCRIPTIONS OF THE DRAWINGS

FIG. 1 shows the chemical structure and 1H NMR of a disclosed compound, (4S)-4-{[3-({4-[({[(1R,3aS,3bS,7S,9aR,9bS,11aR)-9a,11a-dimethyl-1-[(2R)-6-methylheptan-2-yl]-1H,2H,3H,3aH,3bH,4H,6H,7H,8H,9H,9aH,9bH,10H,11H,11aH-cyclopenta[a]phenanthren-7-yl]oxy}carbonyl)amino]butyl}amino)propyl]carbamoyl}-4-[(4-{[(2,4- diaminopteridin-6-yl)methyl](methyl)amino}phenyl)formamido]butanoic acid, according to one embodiment of the disclosure.

DETAILED DESCRIPTION OF THE INVENTION

Figure 1:
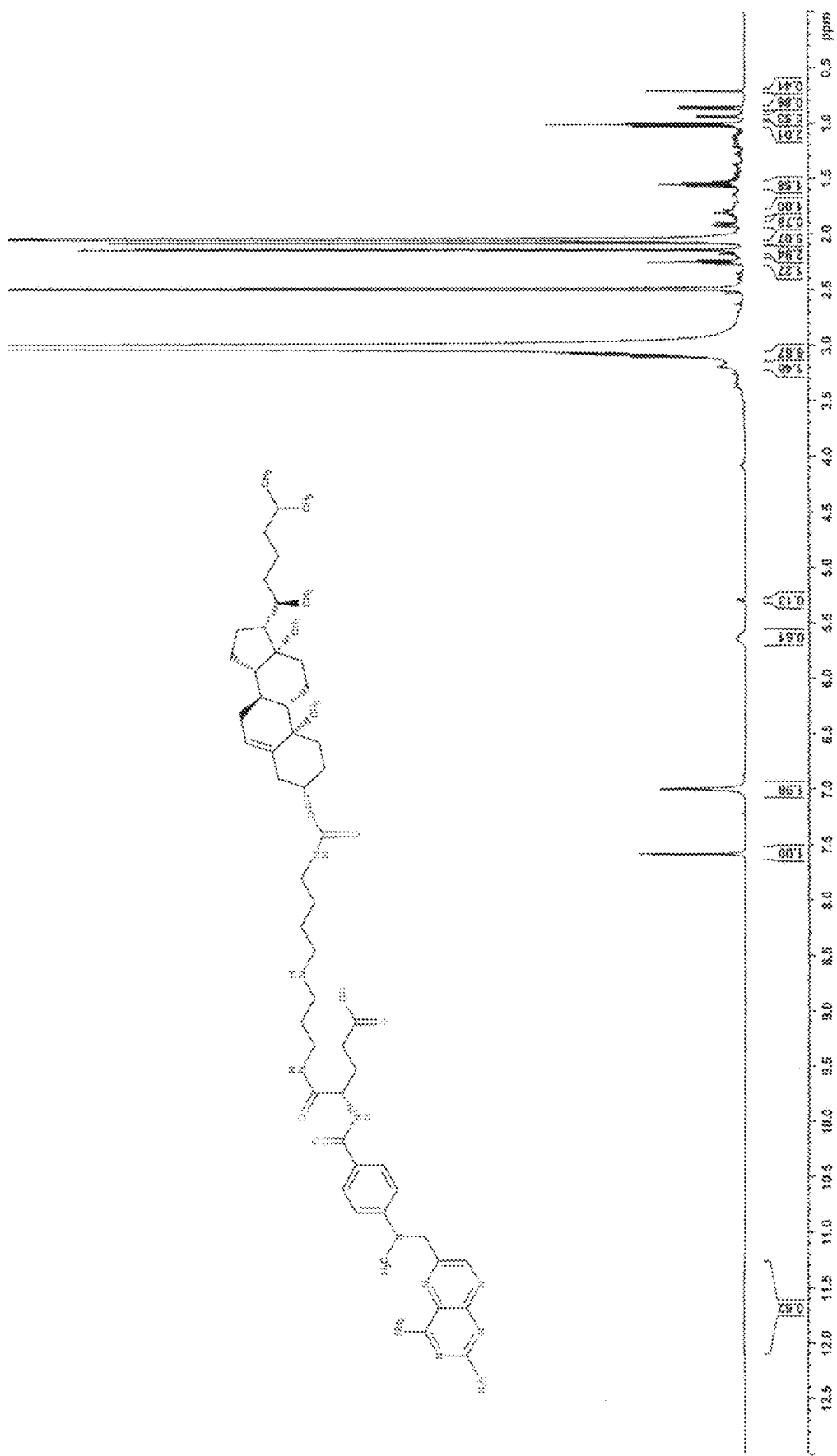

Various aspects of the present invention are described in detail in the following, each attached as an individual Example. The Examples are provided for the purpose of illustration and are not intended to limit the scope of the present invention.

This invention relates to molecule and methods of treating diseases and disorders utilizing a Compound: (4S)-4-{[3-({4-[({[(1R,3aS,3bS,7S,9aR,9bS,11aR)-9a,11a-dimethyl-1-[(2R)-6-methylheptan-2-yl]-1H,2H,3H,3aH,3bH,4H,6H,7H,8H,9H,9aH,9bH,10H,11H,11aH-cyclopenta[a]phenanthren-7-yl]oxy}carbonyl)amino]butyl}amino)propyl]carbamoyl}-4-[(4-{[(2,4-diaminopteridin-6-yl)methyl](methyl)amino}phenyl)formamido]butanoic acid and pharmaceutically acceptable salts, hydrates, solvates, clathrates, prodrugs and polymorphs thereof.

The present invention encompasses the in vitro and in vivo use of the said compound and the incorporation of the said compound into pharmaceutical compositions for the treatments and preventions of a variety of diseases and disorders. Such treatments include, particularly, the inhibition of tumor cell proliferation, the treatment or prevention of cancer, including, but not limited to, solid tumors, blood-born tumors, leukemias, and in particular, acute lymphoblastic leukaemia (ALL).

The present invention encompasses the in vitro and in vivo use of the said compound and the incorporation of the said compound into pharmaceutical compositions for the treatments and preventions of a variety of diseases and disorders. Such treatments include, particularly, the inhibition of an inflammation in autoimmune disease, including, but not limited to, rheumatoid arthritis, systemic lupus erythematosus (SLE), psoriasis, pemphigus, pemphigoid, sarcoidosis, vitiligo.

The pharmaceutical composition comprising the disclosed compound is adjunctively administered with at least one additional therapeutic agent. Examples of additional therapeutic agents include, but are not limited to, anti-cancer drugs, anti-inflammatories, antihistamines, and decongestants.

According to one aspect of the disclosure, a pharmaceutical compound comprising a first component as methotrexate and a second component as cholesterol is disclosed, wherein the first component is covalently conjugated to the second component having a structure represented by the following chemical formula (I):

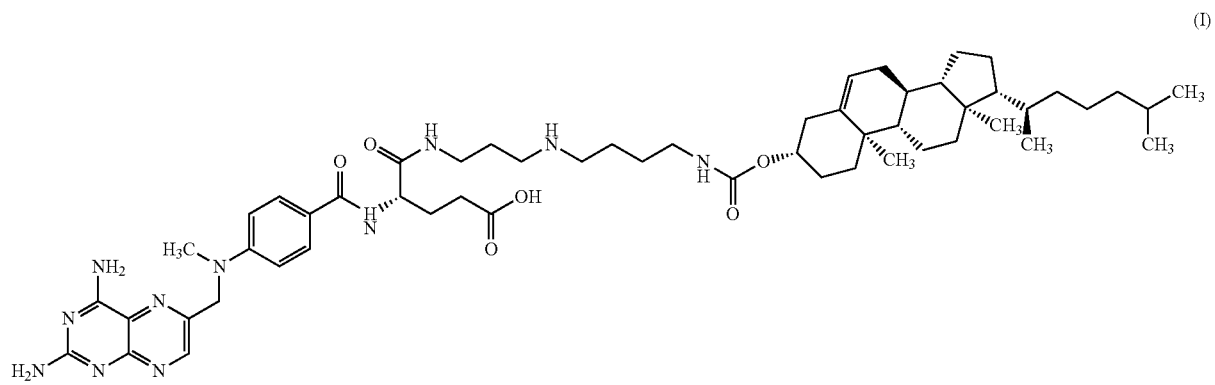 [SMILES: CC(C)CCC[C@@H](C)[C@H]1CC[C@H]2[C@@H]3CC=C4C[C@@H](OC(=O)NCCCCNCCCNC(=O)[C@H](CCC(=O)O)NC(=O)c5ccc(N(C)Cc6cnc7nc(N)nc(N)c7n6)cc5)CC[C@]4(C)[C@H]3CC[C@]12C]

(I)

wherein the α carboxyl group of methrotrexate is conjugated to cholesterol using spermidine as a linker.

In some embodiments, a pharmaceutical compound comprising a compound as defined above and a pharmaceutically acceptable carrier, excipient and/or adjuvant is provided.

In one exemplification, the synthesis of the disclosed compound which is a methrotrexate-spermidine-cholesterol conjugate, (4S)-4-{[3-({4-[({[(1R,3aS,3bS,7S,9aR,9bS,11aR)-9a,11a-dimethyl-1-[(2R)-6-methylheptan-2-yl]-1H,2H,3H,3aH,3bH,4H,6H,7H,8H,9H,9aH,9bH,10H,11H,11aH-cyclopenta[a]phenanthren-7-yl]oxy}carbonyl)amino]butyl}amino)propyl]carbamoyl}-4-[(4-{[(2,4-diaminopteridin-6-yl)methyl](methyl)amino}phenyl)formamido]butanoic acid, utilizes an activation of the hydroxyl group and follows Scheme A. Cholesterol (1.93 g, 5 mmol) and 1,1'-Carbonyldiidazole (CDI) (as disclosed by Greg T. Hermanson., Bioconjugate. 2013, p 229) which were suspended in dimethyl sulfoxide (DMSO)(10 ml). was mixed. The mixture obtained was incubated to form active substances for 1 hour at room temperature. After 1 hour of incubation, spermidine (0.73 g, 5 mmol) was added to the mixtures. Subsequently, all mixtures were incubated at room temperature overnight. Reaction Scheme B, Methotrexate (2.27 g, 5 mmol) and 1-(3-Dimethylaminopropyl)-3-ethylcarbodiimide (0.96 g, 5 mmol) were suspended in DMSO. Then, the mixtures from the Scheme A were added to the solution and incubated for 24 hours at room temperature. The new product was purified by flash chromatography on silica column. The purified product was further dried in vacuo, resulting a yellowish material, the final yield was 3.25 g (65.92%) ES(−)-MS: M-994.4.

According to another aspect of the disclosure, the use of the compound as defined above in medicine, such as the use of the embodied compound in a medicament, is provided herein. In some embodiments, the medicament including the compound as defined herein is suitable for treating mammals, such as a human. Moreover, another aspect of the disclosure includes the use of the compound as defined above for the manufacture of a medicament for the treatment of a cancer comprising cancer cells, wherein the examples of the cancer include leukemia, lymphoma, breast, lung, cervical, brain, and other hematologic cancer. In addition, another aspect of the disclosure includes the use of the compound as defined above for the manufacture of a medicament for the treatment of connective tissue and autoimmune disease, wherein the examples of connective tissue and autoimmune diseases include systemic lupus erythematosus (SLE), psoriasis, pemphigus, pemphigoid, sarcoidosis, vitiligo.

Further examples of the tests of the composition comprising the disclosed compound will now be described.

Example 1: Dihydrofolate Reductase Inhibitor Assay of Embodied Compound and MTX

Embodied compound (compound A) and MTX at final concentrations 5, 50, 50 nM were tested for DHFR inhibiting activity with Dihydrofolate reductase (DHFR) assay kit (Sigma-Aldrich, Mo., USA). According to the supplier protocol, the activity of DHFR reductase was measured at 340 nM, every 15 seconds for 2.5 minutes, with the Biochrom Anthos 2010 microplate reader (Biochrom Ltd., Cambourne, Cambridge, UK). The enzymatic activity was calculated by the following formula:

$$\text{Units}/\text{mg}P = \frac{(\Delta OD/\text{min sample} - \Delta OD/\text{min blank}) \times d}{12.3 \times V \times \text{mg}P/\text{ml}}$$

Figure 2:
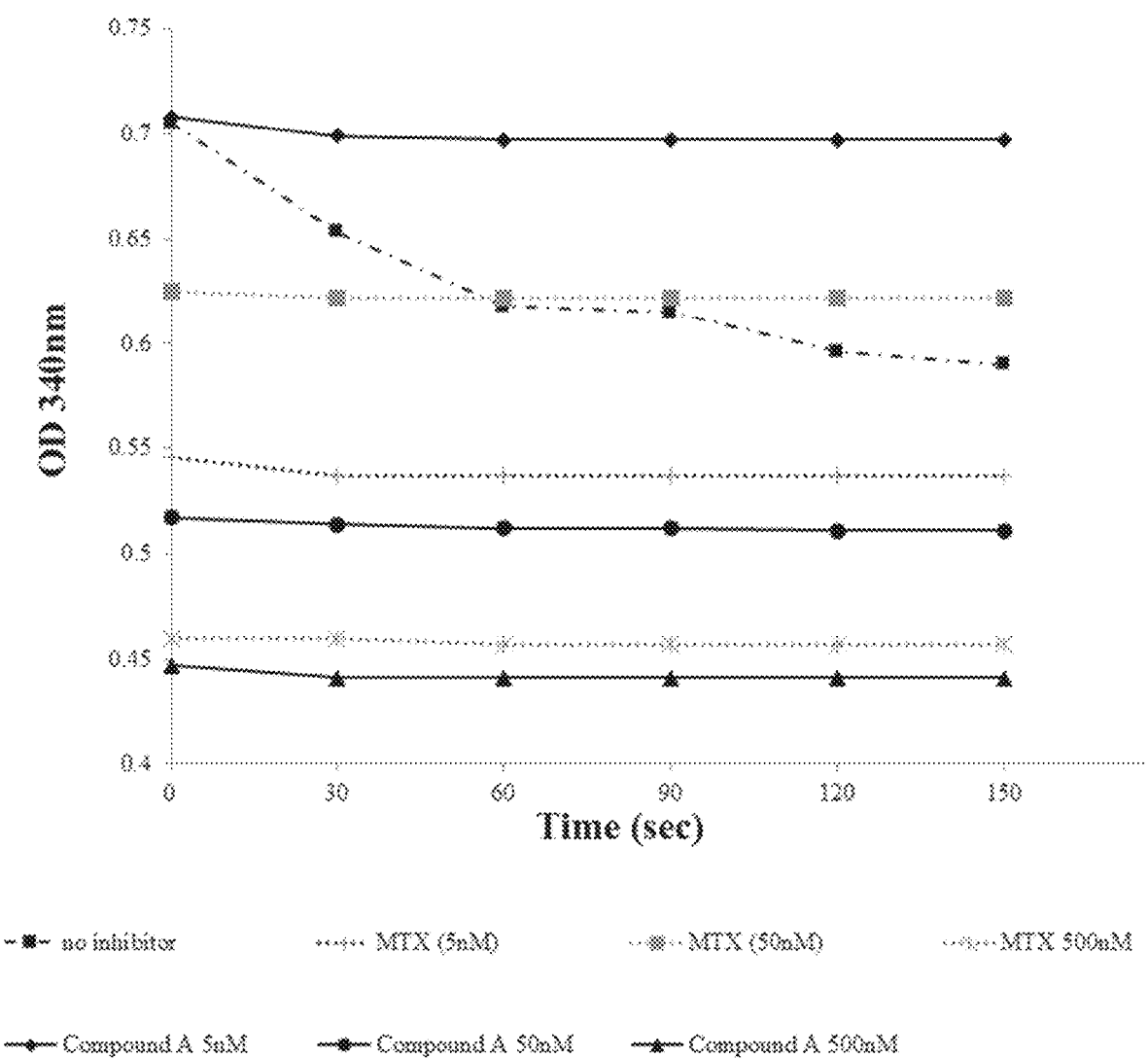
FIG. 2 shows inhibitory effect on dihydrofolate reductase enzyme of a compound according to one embodiment of the disclosure (compound A).

$\Delta OD/\text{min blank} = \Delta OD/\text{min.}$ for the blank $\Delta OD/\text{min sample} = \Delta OD/\text{min.}$ for the reaction $12.3 = $ Extinction coefficient($\Delta$, $mM^{-1}cm^{-1}$) for the $DHFR$ reaction at 340 nm $V = $ Enzyme volume in ml used in the assay $d = $ The dilution factor of enzyme sample $\text{mg}P/\text{ml} = $ Enzyme concentration of the original sample before dilution $\text{Units}/\text{mg}P = $ Specific activity in $\mu\text{mole}/\text{min}/\text{mg}$ protein The changing of OD 340 is shown in FIG. 2 and the enzymatic activities are shown in Table 1.

TABLE 1

Dihydrofolate reductase activity

| | Dihydrofolate reductase (DHFR) activity | |
|---|---|---|
| | Unit/mgP | % |
| No inhibitor | 14.998 | 100 |
| MTX 5 mM | 0.981 | 6.54 |

TABLE 1-continued

Dihydrofolate reductase activity

| | Dihydrofolate reductase (DHFR) activity | |
|---|---|---|
| | Unit/mgP | % |
| MTX 50 mM | 0.14 | 0.93 |
| MTX 500 mM | 0.14 | 0.93 |
| Embodied compound 5 mM | 1.261 | 8.41 |
| Embodied compound 50 mM | 0.561 | 3.74 |
| Embodied compound 500 mM | 0.561 | 3.74 |

Figure 3A:
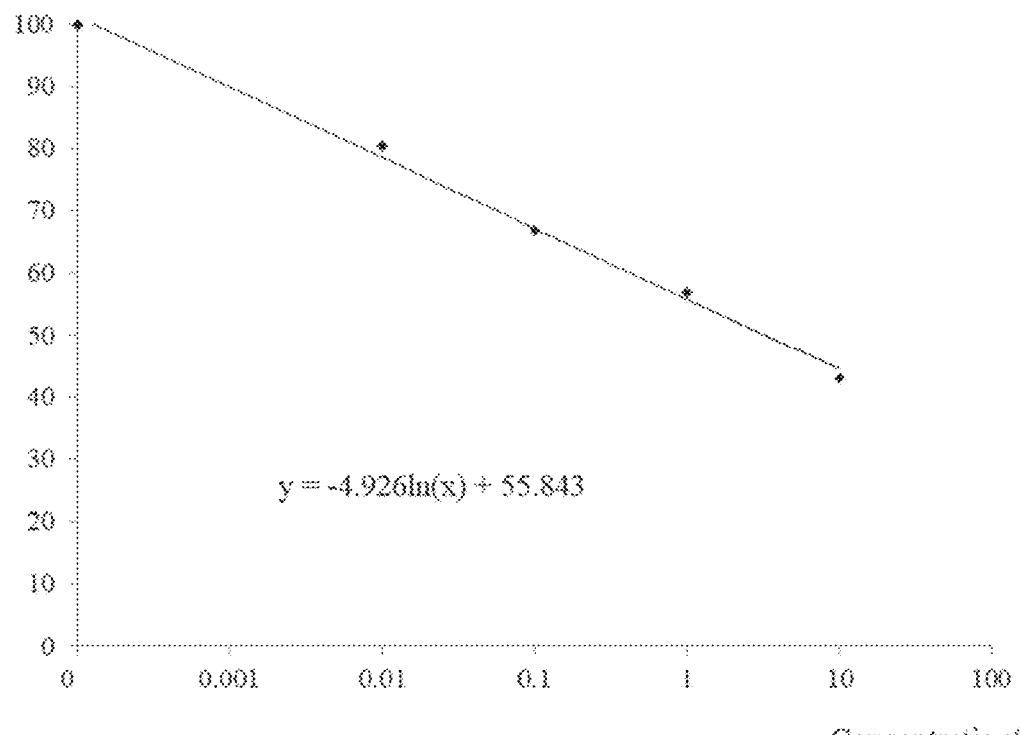
FIG. 3 shows cytotoxicity of MTX (3A.) and a compound according to one embodiment of the disclosure (3B.).
Figure 3B:
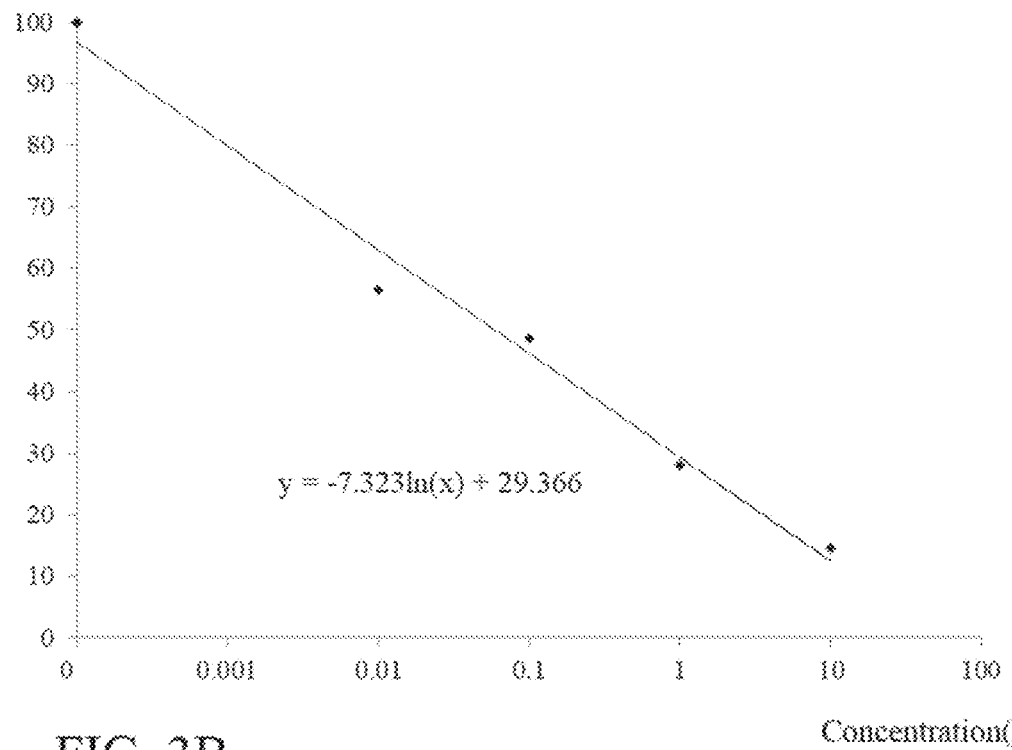

Example 2:
3-(4,5-dimethylthiazol-2-yl)-2,5-diphenyl Tetrazolium Bromide (MTT) Assay for Cytotoxicity Effect of Embodied Compound on Tumor Cells The human breast cancer cell line, MCF-7, was obtained from American Type Cell Collection (ATCC) (Rockville, Mo., U.S.A.). The cells were cultured to 70-80% confluence in Dulbecco's modified Eagle medium (DMEM) (Gibco, Grand Island, N.Y., U.S.A.) with 10% fetal bovine serum (FBS) (Gibco) at 37° C. and 5% CO2. MCF-7 cells were plated overnight in a 96-well plate (4,000 cells per well). Cells were treated with either embodied compound or MTX at a final concentration 0, 0.01, 0.1, 1 and 10 mM for 24 hours. Next, 10 μl/well of WST-1/ECS solution from the Quick Cell Proliferation Colorimetric Assay Kit (BioVision, Inc., Milptas, Calif., U.S.A.) was added, and the solution was incubated for 2 hours at 37° C. and 5% CO2. Absorbance was measured at 480 nm with the Biochrom Anthos 2010 microplate reader (Biochrom Ltd., Cambourne, Cambridge, UK). The half maximal inhibitory concentrations (IC50) were calculated from log-linear regression from the absorbance optical density (OD). The IC50 of MTX is 3.27 mM, whereas the IC50 of embodied compound is 0.06 mM. The 24 h cell viability is shown in FIG. 3A for MTX and FIG. 3B for embodied compound.

Example 3: Lipid Solubility and Oil in Water (O/W) Emulsion Analysis

Figure 4:
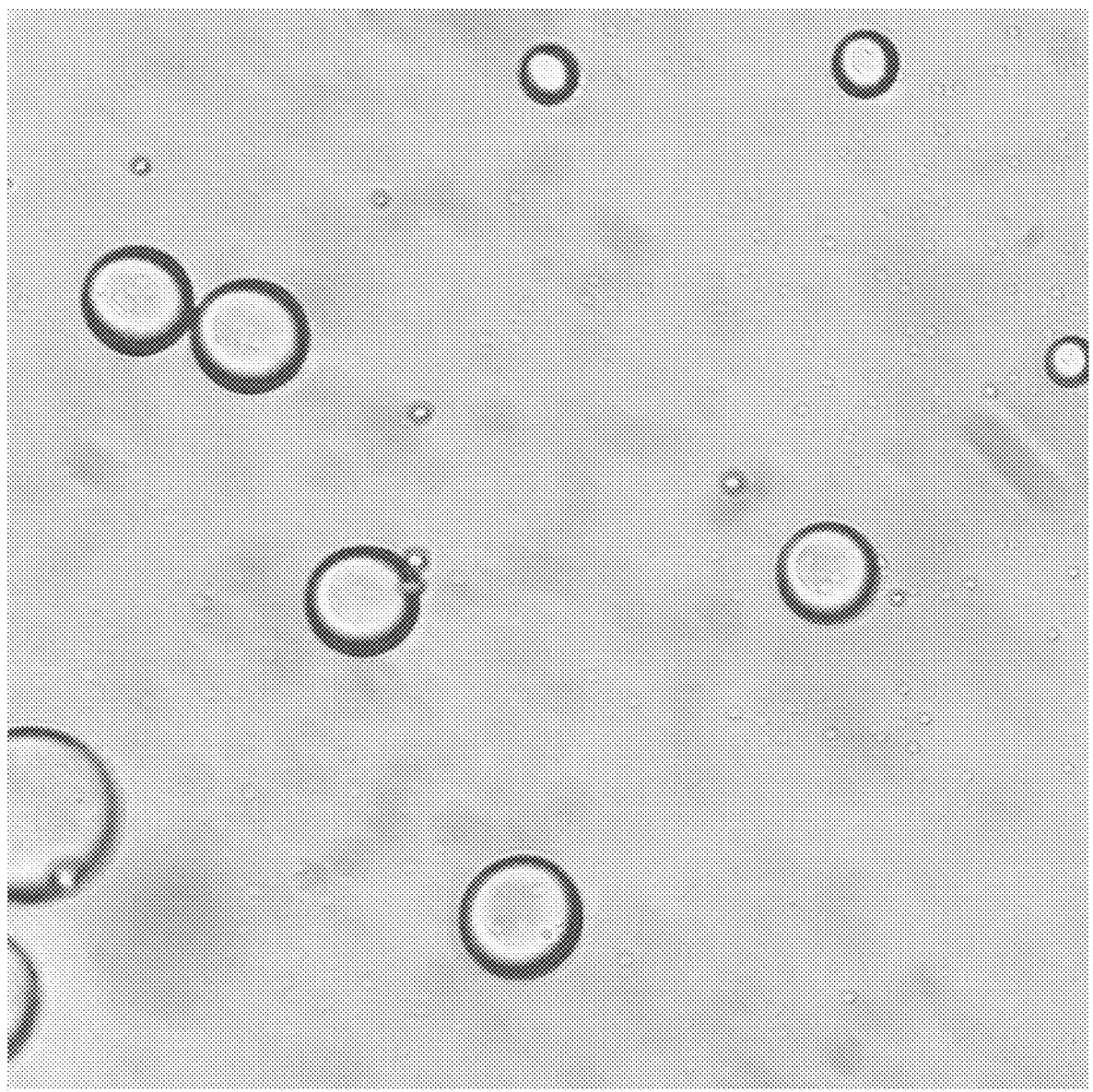
FIG. 4 shows an image of embodied compound in O/W droplets, visualized under light microscopy.

Embodied compound or Methrotrexate in DMSO (3 μg/μl) were dissolved in olive oil, canola oil and sunflower oil(Sigma-Aldrich (St. Louis, Mo., USA)) at 40° C. The suspended were vortexed and centrifuged at 3000 RPM, 10 mins periodically. Oil solvent volume was stepwise increased till completely soluble was observed and the soluble concentration were determined (Table 2). The solutions were left at 24° C. overnight and were centrifuged at 5000 RPM for 20 mins. Ten microliter of embodied compound in oils were added to 100 μl deionized (DI) water. The suspensions were vigorously vortex and left at room temperature. The distribution of embodied compound in O/W droplets were visualized under light microscope (as shown in FIG. 4). FIG. 4 shows an image of embodied compound in O/W droplets, visualized under light microscopy.

TABLE 2

| | Solubility in Oil (40° C.) | |
|---|---|---|
| | Disclosed compound (mg/100 ml) | Methrotrexate (mg/100 ml) |
| Olive Oil | 48.1 | less than 0.1 |
| Canola Oil | 81.3 | less than 0.1 |
| Sunflower Oil | 103.6 | less than 0.1 |

The foregoing description of the present invention has been presented for the purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

The invention claimed is:

1. A pharmaceutical compound comprising a first component as methotrexate and a second component as cholesterol, wherein the first component is covalently conjugated to the second component having a structure represented by the following chemical formula (I):

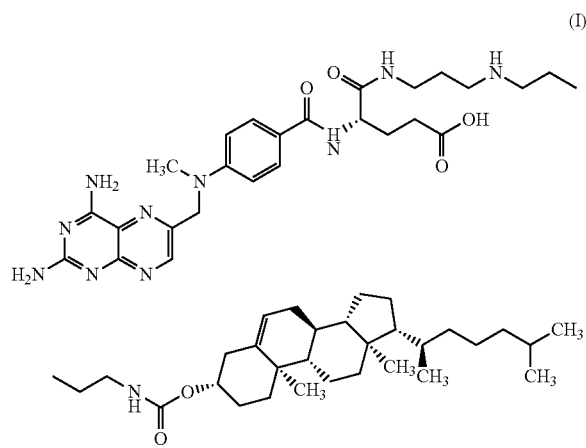

wherein the double lines indicate the bond that connects the first part of formula (I) to the second part, wherein α carboxyl group of methotrexate is conjugated to cholesterol using spermidine as a linker, and a pharmaceutically acceptable salt thereof.

2. A pharmaceutical composition comprising a compound as defined in claim 1 and a pharmaceutically acceptable carrier, excipient and/or adjuvant.

3. Method of treating an indication treatable with methotrexate by administering the compound as defined in claim 1.

4. Method of treating an indication treatable with methotrexate by administering the composition as defined in claim 2.

5. Method of treating a cancer comprising cancer cells or an autoimmune disease by administering the compound as defined in claim 1.

6. The method of treatment according to claim 5, wherein the cancer is breast cancer, lung cancer, multiple myeloma, malignant melanoma, malignant glioma, lymphoma, leukemia, or other hematologic malignancy.

7. The method of treatment according to claim 5, wherein the autoimmune disease is rheumatoid arthritis, systemic lupus erythematosus (SLE), psoriasis, pemphigus, pemphigoid, sarcoidosis, or vitiligo.

8. Method of treating a cancer comprising cancer cells or an autoimmune disease by administering the compound as defined in claim 2.

9. The method of treatment according to claim 8, wherein the cancer is breast cancer, lung cancer, multiple myeloma, malignant melanoma, malignant glioma, lymphoma, leukemia, or other hematologic malignancy.

10. The method of treatment according to claim 9, wherein the autoimmune disease is rheumatoid arthritis, systemic lupus erythematosus (SLE), psoriasis, pemphigus, pemphigoid, sarcoidosis, or vitiligo.

11. The method of treatment according to claim 3, wherein the administering is to a mammal.

12. The method of treatment according to claim 4, wherein the administering is to a mammal.

13. The method of treatment according to claim 5, wherein the administering is to a mammal.

14. The method of treatment according to claim 6, wherein the administering is to a mammal.

15. The method of treatment according to claim 7, wherein the administering is to a mammal.

16. The method of treatment according to claim 8, wherein the administering is to a mammal.

17. The method of treatment according to claim 9, wherein the administering is to a mammal.

18. The method of treatment according to claim 10, wherein the administering is to a mammal.

19. The method of treatment according to claim 11, wherein the mammal is a human.

20. The method of treatment according to claim 13, wherein the mammal is a human.

* * * * *